(12) United States Patent
Prakash et al.

(10) Patent No.: US 6,642,406 B2
(45) Date of Patent: Nov. 4, 2003

(54) SYNTHESIS OF N-[N-(3,3-DIMETHYLBUTYL)-L-α-ASPARTYL]-L-PHENYLALANINE 1-METHYL ESTER USING L-α-ASPARTYL-L-PHENYLALANINE 1-METHYL ESTER PRECURSORS

(75) Inventors: Indra Prakash, Hoffman Estates, IL (US); Zhi Guo, Mount Prospect, IL (US); Steve Schroeder, Belvidere, IL (US); Kurt L. Wachholder, Elgin, IL (US)

(73) Assignee: The NutraSweet Company, Chicago, IL (US)

( * ) Notice: Subject to any disclaimer, the term of this patent is extended or adjusted under 35 U.S.C. 154(b) by 27 days.

(21) Appl. No.: 09/859,438

(22) Filed: May 18, 2001

(65) Prior Publication Data

US 2002/0019557 A1 Feb. 14, 2002

Related U.S. Application Data

(60) Provisional application No. 60/205,105, filed on May 18, 2000.

(51) Int. Cl.[7] .................. C07C 229/00; C07C 271/00
(52) U.S. Cl. .................. 560/40; 560/24; 560/32; 560/33
(58) Field of Search .................. 560/40, 24, 32, 560/33; 564/473

(56) References Cited

U.S. PATENT DOCUMENTS

| 4,946,988 A | * | 8/1990 | Hill et al. | |
| 5,266,719 A | | 11/1993 | Kishimoto et al. | ........... 500/41 |
| 5,480,668 A | | 1/1996 | Nofre et al. | ................ 426/548 |
| 5,510,508 A | | 4/1996 | Claude et al. | ................ 560/41 |
| 5,728,862 A | | 3/1998 | Prakash | ....................... 560/40 |

FOREIGN PATENT DOCUMENTS

| WO | | 00/15656 | 3/2000 |
| WO | WO 00/15656 A1 | * | 3/2000 |

OTHER PUBLICATIONS

Anderson et al, Azetidines III. A Convenient sysnthesis of 1–Alkyl–3,3–Dimethylazetidines, Journal of Organic Chemistry 1968, 33(5), pp. 2123–2136.*

* cited by examiner

*Primary Examiner*—Johann Richter
*Assistant Examiner*—Paul A Zucker
(74) *Attorney, Agent, or Firm*—Fitzpatrick, Cella, Harper & Scinto

(57) ABSTRACT

N-[N-(3,3-dimethylbutyl)-L-α-aspartyl]-L-phenylalanine 1-methyl ester is produced by hydrogenation of a mixture of 3,3-dimethylbutyraldehyde and a precursor of L-α-aspartyl-L-phenylalanine 1-methyl ester. In particular, N-[N-(3,3-dimethylbutyl)-L-α-aspartyl]-L-phenylalanine 1-methyl ester is produced using an acid salt of L-α-aspartyl-L-phenylalanine 1-methyl ester or N-protected L-α-aspartyl-L-phenylalanine 1-methyl ester. The production method is efficient and low cost, as compared with conventional N-[N-(3,3-dimethylbutyl)-L-α-aspartyl]-L-phenylalanine 1-methyl ester synthesis.

35 Claims, No Drawings

SYNTHESIS OF N-[N-(3,3-DIMETHYLBUTYL)-L-α-ASPARTYL]-L-PHENYLALANINE 1-METHYL ESTER USING L-α-ASPARTYL-L-PHENYLALANINE 1-METHYL ESTER PRECURSORS

This application claims the benefit of U.S. Provisional Patent Application No. 60/205,105, filed May 18, 2000.

BACKGROUND OF THE INVENTION

1. Field of the Invention

This invention relates to the synthesis of N-[N-(3,3-dimethylbutyl)-L-α-aspartyl]-L-phenylalanine 1-methyl ester (neotame) using L-α-aspartyl-L-phenylalanine 1-methyl ester (aspartame) precursors. This method of producing neotame results in high purity and is more simple and more economical than the conventional preparation of neotame.

2. Related Background Art

N-[N-(3,3-dimethylbutyl)-L-α-aspartyl]-L-phenylalanine 1-methyl ester (neotame) is a high potency dipeptide sweetener (about 8000× sweeter than sucrose) that has the formula

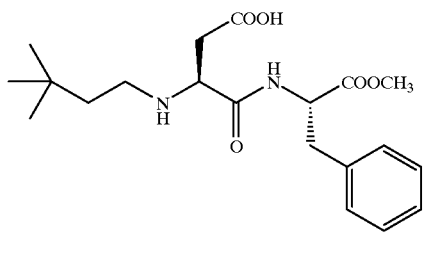

Neotame

The chemical synthesis of neotame is disclosed in U.S. Pat. Nos. 5,480,668, 5,510,508, 5,728,862 and WO 00/15656, the disclosure of each of which is incorporated by reference herein.

U.S. Pat. Nos. 5,510,508 and 5,728,862 describe the synthesis of neotame by hydrogenation of a mixture of aspartame and 3,3-dimethylbutyraldehyde with a catalyst such as Pd on carbon. This synthesis is represented by the following equation.

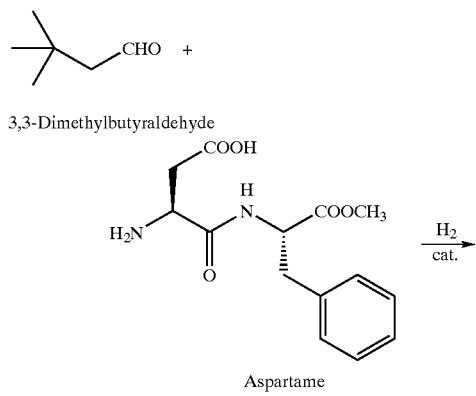

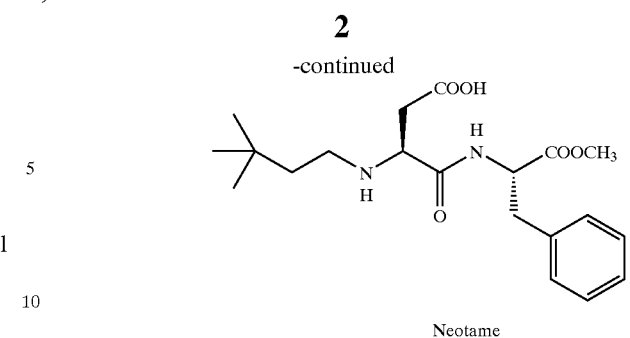

Neotame

The aspartame used in this synthesis is produced by its precursors. For example, aspartame may be produced by neutralization of aspartame hydrochloride followed by crystallization as described in U.S. Pat. No. 5,266,719, the disclosure of which is incorporated by reference herein. Such a neotame process requires the reaction of pure isolated aspartame with the aldehyde to produce neotame. Therefore, it would be economically advantageous to use aspartame precursors directly in neotame synthesis without having to first isolate aspartame.

International Patent Publication No. WO 00/15656 attempts to eliminate some of these complicated process steps. WO 00/15656 describes the formation of neotame by hydrogenation of a mixture of 3,3-dimethylbutyraldehyde and Z-aspartame (N-benzyloxycarbonyl-L-α-aspartyl-L-phenylalanine-1-methyl ester) in a methanolic solvent.

WO 00/15656 discloses that the neotame obtained by this method has a purity as low as 87% with significant amounts of known and unknown impurities.

Since neotame is mainly employed in foods for human consumption, it is extremely important that neotame exist in a highly purified state. Any impurity >0.1% must be structurally characterized and subjected to safety studies. In this regard, it is clear that the neotame produced by the method of WO 00/15656 is not acceptable with respect to purity.

Thus, it is clear that there is a need to economically and efficiently produce pure N-[N-(3,3-dimethylbutyl)-L-α-aspartyl]-L-phenylalanine 1-methyl ester.

SUMMARY OF THE INVENTION

The present invention relates to the efficient, low cost and high purity synthesis of N-[N-(3,3-dimethylbutyl)-L-α-aspartyl]-L-phenylalanine 1-methyl ester (neotame). According to one embodiment of the present invention, neotame is synthesized by reacting an acid salt of aspartame and 3,3-dimethylbutyraldehyde in a solvent or a mixture of solvents under hydrogenation conditions with a catalyst. The acid salt of aspartame may be an isolated compound or its wet cake. In certain preferred embodiments, hydrobromic, sulfuric, phosphoric, citric, acetic or hydrochloric acid salts of aspartame are employed.

In a second embodiment of the present invention, neotame is synthesized by hydrogenating a mixture of N-protected aspartame and 3,3-dimethylbutyraldehyde in a solvent or a mixture of solvents with a catalyst. The protecting groups are those that can be cleaved by hydrogenolysis. They include, without limitation, carbamate, amides, benzylidenes, benzyl and silyl.

DETAILED DESCRIPTION

The present invention relates to the synthesis of N-[N-(3,3-dimethylbutyl)-L-α-aspartyl]-L-phenylalanine 1-methyl ester (neotame) by hydrogenation of a mixture of 3,3- dimethylbutyraldehyde and a precursor of L-α-aspartyl-L-phenylalanine 1-methyl ester (aspartame) with a catalyst. More specifically, an acid salt of aspartame (isolated or generated in situ) or protected aspartame is used to produce neotame, thereby eliminating the need to isolate aspartame prior to its combination with 3,3-dimethylbutyraldehyde.

According to the first embodiment of the present invention, N-[N-(3,3-dimethylbutyl)-L-α-aspartyl]-L-phenylalanine 1-methyl ester is synthesized by reacting an acid salt of L-α-aspartyl-L-phenylalanine 1-methyl ester and 3,3-dimethylbutyraldehyde in a solvent or a mixture of solvents under hydrogenation conditions, i.e., in the presence of hydrogen, with a catalyst. Optionally, the acid salt of L-α-aspartyl-L-phenylalanine 1-methyl ester is pretreated with a base; alternatively, a base is included in the reaction mixture.

Suitable acid salts of aspartame include, without limitation, hydrobromic, sulfuric, phosphoric, citric, acetic and hydrochloric acid salts of L-α-aspartyl-L-phenylalanine 1-methyl ester. The acid salt of aspartame used in the present inventive process can be a wet cake or a dry cake. The acid salt of aspartame can also be used in situ from its precursors by the acidic hydrolysis of an N-protected aspartame, for example, by treatment of N-formyl aspartame, N-BOC aspartame or other N-protected aspartame with HCl or another acid. The N-protected aspartame may be, without limitation, acetyl, benzoyl, benzyloxycarbonyl, (p-chlorobenzyl)oxycarbonyl, (p-bromobenzyl)oxycarbonyl, (p-nitrobenzyl)oxycarbonyl, tert-butyloxycarbonyl, formyl, (p-methoxybenzyl)oxycarbonyl (MOZ) or p-toluene sulfonyl (Ts). One of ordinary skill in the art would readily recognize that both the meta- and ortho-forms of the above-listed para-groups are also suitable for use in the present invention.

Generally the concentration of the acid salt of aspartame in the solvent is in a range of about 2% to about 20%, more preferably about 7% to about 15%.

The acid salt of aspartame is optionally pre-treated with a base. Suitable bases include, without limitation, sodium carbonate, potassium carbonate and ammonium hydroxide. Alternatively, a base may be included in the reaction mixture. The base may be used in amount of about 0.80 to about 1.2 equivalent of the acid in the acid salt of aspartame.

According to the second embodiment of the present invention, N-[N-(3,3-dimethylbutyl)-L-α-aspartyl]-L-phenylalanine 1-methyl ester is synthesized by reacting an N-protected L-α-aspartyl-L-phenylalanine 1-methyl ester intermediate, 3,3-dimethylbutyraldehyde and a catalyst in a solvent or a mixture of solvents in the presence of hydrogen to produce N-[N-(3,3-dimethylbutyl)-L-α-aspartyl]-L-phenylalanine 1-methyl ester.

The N-protected aspartame suitable for hydrogenolysis use in the present invention comprises a protecting group. Suitable protecting groups include, without limitation, carbamates such as benzyloxycarbonyl, (p-chlorobenzyl)oxycarbonyl, (p-bromobenzyl)oxycarbonyl,(p-methoxybenzyl)oxycarbonyl (MOZ), (p-nitrobenzyl)oxycarbonyl, formyl, benzyl and silyl.

The N-protected aspartame used in the present inventive process can be a wet cake or a dry cake. Protected aspartame can be prepared by any known chemical or enzymatic method.

Generally the concentration of the N-protected aspartame in the solvent is in a range of about 2% to about 20%, more preferably about 7% to about 15%.

Solvents suitable for use in either embodiment of the present invention include, without limitation, ethanol, ethyl acetate, acetonitrile, dioxane, methanol, isopropanol, isobutyl methyl ketone, tetrahydrofuran, cyclohexane, toluene, dimethylformamide (DMF), water and mixtures thereof. The solvent can be added to a dry cake of an acid salt of aspartame or N-protected aspartame. Alternatively, the solvent may be used in situ in the formation of an acid salt of aspartame or N-protected aspartame, or it may be added to a reaction mixture.

The catalyst suitable for use in either embodiment of the present invention may be selected from catalysts based on palladium or platinum including, without limitation, platinum on activated carbon, palladium on activated carbon, platinum black or palladium black. Other catalysts include, without limitation, nickel on silica, nickel on alumina, Raney nickel, ruthenium black, ruthenium on carbon, palladium hydroxide on carbon, palladium oxide, platinum oxide, rhodium black, rhodium on carbon and rhodium on alumina. The catalysts based on palladium or platinum are preferred.

The catalyst is present in an amount effective to produce neotame in an acceptable rate and yield. Generally, the weight ratio of catalyst (on a dry basis) to aspartame is about 0.01:1 to about 0.25:1, preferably about 0.10:1. It is important to note that about a 10% catalyst loading is required to minimize the undesirable yield of dialkylated aspartame.

3,3-Dimethylbutyraldehyde is a readily available starting material. According to the present invention, 3,3-dimethylbutyraldehyde can be added slowly or all at once to the reaction mixture. When the aldehyde is gradually added, typically it is added over the course of about 2 to 8 hours, preferably from about 4 to 6 hours.

3,3-Dimethylbutyraldehyde and the aspartame precursor are typically combined in a substantially equivalent molar ratio, i.e., about 1:0.95 to 1:1. Excess molar amounts of aspartame are not preferred due to waste and cost. Higher molar amounts of the aldehyde are likely to lead to the generation of impurities. Further, the 3,3-dimethylbutyraldehyde used in the present process should be highly pure. Small impurities in the 3,3-dimethylbutyraldehyde may produce odor. Higher molar ratios of aldehyde may cause the entrapment of the aldehyde during subsequent crystallization of neotame and produce odor; alternatively, excess aldehyde may be oxidized to the corresponding t-butyl acetic acid which also produces odor. The odor can be removed by washing the final product with organic solvents (such as heptane, ethyl acetate, t-butylmethyl ether, hexane, etc.) or by extruding the final product. The excess aldehyde may also react with neotame to give dialkylated imidazolidinone. This may also be ultimately crystallized along with neotame and will hydrolyze to give neotame and aldehyde.

3,3-Dimethylbutyraldehyde and the acid salt of aspartame or the N-protected aspartame are reacted for a time and at a temperature sufficient to produce neotame. Generally, the time ranges from about 1 to about 24 hours, preferably from about 2 to about 4 hours after addition of the 3,3-dimethylbutyraldehyde is complete. If the 3,3-dimethylbutyraldehyde is added to the reaction mixture all at once, then the time sufficient to produce neotame preferably ranges from about 6 to about 24 hours. Generally, the temperature sufficient to produce neotame according to the present invention ranges from about 20° C. to about 60° C., preferably from about 22° C. to about 40° C.

The reactions of the present invention are carried out in the presence of hydrogen. Generally, the pressure of the hydrogen ranges from about 5 psi to about 100 psi, preferably from about 30 psi to about 50 psi.

Either of the above-described embodiments may also include additional steps. Such additional steps include, without limitation, catalyst removal, solvent concentration adjustment, holding, seeding, cooling (crystallization), and neotame isolation.

The catalyst may be separated by a variety of solid-liquid separation techniques that include, without limitation, the use of sparkler, crossflow, nutsche, basket, belt, disc, drum, cartridge, candle, leaf and bag filters. Furthermore, catalyst separation performance may be enhanced through the use of gravity, pressure, vacuum and/or centrifugal force. Additionally, the catalyst separation rate and removal efficiency may be enhanced through the use of any number of various filter media that include, without limitation, woven cloth fabrics, woven metal fabrics, porous metal substrates and synthetic or naturally occurring membranes. The separation device and media can be permanent, replaceable or disposable. The catalyst solid alone may be separated, or separation may be assisted by the use of porous cellulosic fiber or diatomaceous silica type filter aids, which are used as a media precoat and/or directly with a catalyst slurry. The separation device can be operated in an automated or manual mode for solid media washing, solid discharging and/or solid and media back flushing. The catalyst can be washed and discharged from the filter media using gas, liquid or mechanical means. The catalyst alone or catalyst with filter aid can be partially or totally recycled for used in subsequent hydrogenation reactions.

The reaction mixture, if water is present, may be held for a time and at a temperature sufficient to hydrolyze dialkylated imidazolidinone to a-neotame and 3,3-dimethylbutyraldehyde. The reaction mixture is generally held for about 0.5–24 hours at a temperature of about 20–50° C. In a preferred embodiment of the present invention, the reaction mixture is held for about 2–4 hours.

Typically crystallization of neotame is accomplished by cooling the mixture to about 0–25° C., preferably to about 5–10° C., over the course of about 0.5–2 hours, preferably about 1–2 hours.

Seeding prior to or during crystallization can initiate a controlled crystal growth rate according to the present invention. Hence, the reaction mixture may optionally be seeded in an amount from 0.0001%–10%, by weight of the N-[N-(3,3-dimethylbutyl)-L-α-aspartyl]-L-phenylalanine 1-methyl ester in the solution, preferably from 0.1% to 1% and most preferably from 0.1% to 0.5%. Seeding is typically performed at 25–35° C. and preferably at 28–30° C.

The reaction mixture or the solution containing neotame may be unstirred or stirred according to any embodiment of the present invention.

Crystallized neotame may be separated from the solvent solution by a variety of solid-liquid separation techniques that utilize centrifugal force, that include, without limitation, vertical and horizontal perforated basket centrifuge, solid bowl centrifuge, decanter centrifuge, peeler type centrifuge, pusher type centrifuge, Heinkel type centrifuge, disc stack centrifuge and cyclone separation. Additionally, separation may be enhanced by any of pressure, vacuum, and gravity filtration methods, that include, without limitation, the use of belt, drum, nutsche type, leaf, plate, Rosenmund type, sparkler type, and bag filters and filter press. Operation of the neotame solid-liquid separation device may be continuous, semi-continuous or in batch mode. The neotame solid may also be washed on the separation device using various liquid solvents, including, without limitation, water, methanol and mixtures thereof. The neotame solid can also be partially and totally dried on the separation device using any number of gases, including, without limitation, nitrogen and air, to evaporate residual liquid solvent. The neotame solid may be automatically or manually removed from the separation device using liquids, gases or mechanical means by either dissolving the solid or maintaining the solid form.

The neotame synthesized according to the present invention may be purified by any known method including, but not limited to, the following methods. U.S. Pat. No. 5,728,862 outlines a purification method by which neotame is precipitated out of an aqueous/organic solvent solution, wherein the aqueous/organic solvent solution has an amount of organic solvent of about 17% to about 30% by weight. Copending U.S. patent application Ser. No. 09/448,671, filed on Nov. 24, 1999, relates to methods of purifying neotame by crystallization in a variety of organic solvent/aqueous organic solvent mixtures; each of these methods involves the use of an organic solvent and water mixture and solvent distillation. Copending U.S. patent application Ser. No. 09/449,314, filed on Nov. 24, 1999, relates to methods of purifying neotame using chromatography.

The neotame synthesized according to the present invention is the monohydrate, which may be dried to produce an anhydrous form.

The crystallized and isolated neotame solid may be further purified by a variety of drying methods. Such methods are known to those skilled in the art and include, but are not limited to, the use of a rotary vacuum dryer, fluid bed dryer, rotary tunnel dryer, plate dryer, tray dryer, Nauta type dryer, spray dryer, flash dryer, micron dryer, pan dryer, high and low speed paddle dryer and microwave dryer.

The above-described process of the present invention achieves a number of advantages as compared to conventional neotame synthetic routes. In particular, complicated processing steps to isolate aspartame prior to combining it with 3,3-dimethylbutyraldehyde are eliminated. On a manufacturing scale, this results in processing time savings, as well as a significant cost savings.

The Examples which follow are intended as an illustration of certain preferred embodiments of the invention, and no limitation of the invention is implied.

EXAMPLE 1

Aspartame (7.86 g) and methanol (100 ml) were charged to a hydrogenation vessel. The pH was adjusted to 1.3 with 5 ml of 1 N hydrochloric acid, followed by the addition of 3,3-dimethylbutyraldehyde (2.60 g). The vessel was pressure purged with nitrogen (4×), and 0.34 g of 4% palladium on carbon (containing 50% water) was added. After pressure purging the reactor with nitrogen (4×), followed by hydrogen (4×), the mixture was hydrogenated at 50 psig for 12 hours at room temperature. After completion of the reaction, the vessel was pressure purged with nitrogen (4×). The catalyst was removed from the reaction mixture by filtration through powdered cellulose. Methanol (20 ml) was used to rinse the reaction vessel and the filter cake. The filtrate and wash were combined, and methanol was evaporated under reduced pressure. The solution was reduced to 50 ml total volume, and 25 g of deionized water was added. Methanol was again evaporated from the solution under reduced pressure until the methanol content was 25–30%. The crystallized solid was isolated by filtration and washed with 20 ml deionized water. The wet product was dried under vacuum at 40° C. to give 6.5 g neotame (>98% by HPLC).

EXAMPLE 2

Aspartame (11.76 g), tertbutylacetic acid (4.64 g) and methanol (100 ml) were charged to a hydrogenation vessel.

3,3-Dimethylbutyraldehyde (4.0 g) was added. The vessel was pressure purged with nitrogen (4×), and 0.48 g of 4% palladium on carbon (containing 50% water) was added. After pressure purging the reactor with nitrogen (4×), followed by hydrogen (4×), the mixture was hydrogenated at 50 psig for 12 hours at room temperature. After completion of the reaction, the vessel was pressure purged with nitrogen (4×). The catalyst was removed from the reaction mixture by filtration through powdered cellulose. Methanol (50 ml) was used to rinse the reaction vessel and the filter cake. The filtrate and wash were combined, and methanol was evaporated under reduced pressure. The solution was reduced to 75 ml total volume, and 75 g of deionized water was added. The remaining methanol was evaporated from the solution under reduced pressure. The resulting solution was stirred at room temperature for 12 hours. Hexane (75 ml) was added, and the solution was stirred for 3 hours at room temperature. The crystallized solid was isolated by filtration and washed with 50 ml deionized water and 50 ml of hexane. The wet product was dried in air to give 8.1 g of neotame (>98% by HPLC).

EXAMPLE 3

Aspartame (5.88 g), acetic acid (1.20 g) and methanol (100 ml) were charged to a hydrogenation vessel, followed by 3,3-dimethylbutyraldehyde (2.00 g). The vessel was pressure purged with nitrogen (4×), and 0.24 g of 4% palladium on carbon (containing 50% water) was added. After pressure purging the reactor with nitrogen (4×), followed by hydrogen (4×), the mixture was hydrogenated at 50 psig for 12 hours at room temperature. After completion of the reaction, the vessel was purged with nitrogen (4×). The catalyst was removed from the reaction mixture by filtration through powdered cellulose. Methanol (20 ml) was used to rinse the reaction vessel and the filter cake. The combined filtrate and wash was evaporated to dryness. The residue was stirred with 50 ml of deionized water and 50 ml of heptane for 4 hours at room temperature. The crystallized solid was isolated by filtration and washed with 20 ml heptane. The wet product was dried under vacuum at 40° C. to give 7.15 g of neotame (>97% by HPLC).

EXAMPLE 4

Aspartame hydrochloride (15.0 g) containing 27% water was charged to a stirred hydrogenation vessel. The solid was stirred in methanol (80 g) and water (30 g) until dissolved, and the solution was heated to 40° C. One equivalent of NaHCO$_3$ (2.7 g) was added with an additional 10 g of methanol and 30 g of water. After the evolution of gas ceased, the vessel was pressure purged with nitrogen (4×), and 3.94 g of 5% palladium on carbon (containing 62.5% water) was charged to the vessel. The vessel was pressure purged with nitrogen (4×), then with hydrogen (4×). After the final purge, the vessel was pressurized to 50 psig with H$_2$, and 3.2 g of 3,3-dimethylbutyraldehyde was pumped into the reaction over 50 minutes. Hydrogenation continued at 40° C. for 22 hours after addition was completed. The reaction mixture was filtered through powdered cellulose to remove the catalyst. The reaction vessel and catalyst cake were rinsed with 10 g of methanol, and this was combined with the filtrate. Solvent was evaporated under reduced pressure until the methanol was 27% by weight. The solution was heated to 40° C. for 2 hours then cooled to 28° C. At 28° C., the solution was seeded with 0.02 g of neotame crystals. The seeded solution was cooled to 5° C. over 6 hours. The crystalized neotame was filtered and washed twice with 20 ml water. The wet solid was dried under vacuum to give 5.64 g of dry neotame.

EXAMPLE 5

Aspartame hydrochloride (15.0 g) containing 27% water and 3.94 g of 5% palladium on carbon catalyst (containing 62.5% water) were charged to a stirred hydrogenation vessel. The reactor was pressure purged four times with N$_2$. Water (75 g) and methanol (75 g) were added to the reactor, and the solid was stirred at 25° C. until dissolved. The vessel was pressure purged with nitrogen (4×) and then with hydrogen (4×). After the final purge, the vessel was pressurized to 50 psig with H$_2$, and 3.2 g of 3,3-dimethylbutyraldehyde was pumped into the reaction over 60 minutes. Hydrogenation continued at 25° C. for 22 hours after addition was completed. The reaction mixture was filtered through powdered cellulose to remove the catalyst. The reaction vessel and catalyst cake were rinsed with 10 g of methanol, and this was combined with the filtrate. One equivalent of NaHCO$_3$ (2.7 g) was added to neutralize the hydrochloride salt. After the production of gas ceased, solvent was evaporated under reduced pressure until the methanol was 27% by weight. The solution was heated to 40° C. for 2 hours then cooled to 28° C. At 28° C., the solution was seeded with 0.02 g of neotame crystals. The seeded solution was cooled to 5° C. over 6 hours. The crystallized neotame was filtered and washed twice with 20 ml water. The wet solid was dried under vacuum to give 7.41 g of dry neotame.

EXAMPLE 6

Aspartame hydrochloride salt (10 mmol) and 3,3-dimethylbutyraldehyde (10 mmol) were dissolved in methanol (100 ml) in a hydrogenation vessel. Sodium hydrogen carbonate (NaHCO$_3$, 12 mmol) and 5% palladium on carbon (100 mg) were added. The mixture was hydrogenated at 30–40 psi for 2 days at room temperature. After completion of the reaction, the catalyst was removed from the reaction mixture by filtration and washed with methanol (3×20 ml). The combined organic solvent was removed under reduced pressure below 40° C., and the residue was extracted using methylene chloride. The wet product was dried over sodium sulfate, and the solvent was removed in vacuo below 40° C. to give neotame in 90% yield.

EXAMPLE 7

Z-Aspartame (10.0 g) and 5% palladium on carbon catalyst (containing 62% water) (1.33 g) were charged to a hydrogenation vessel. The vessel was pressure purged with nitrogen (4×), and 50 g of deionized water and 50 g of methanol were added. After pressure purging the reactor with nitrogen (4×), followed by hydrogen (4×), the mixture was heated to 40° C. and pressurized to 50 psig with hydrogen. Over a period of one hour, 2.29 g of 3,3-dimethylbutyraldehyde were pumped into the stirred reaction mixture. After addition of the aldehyde, hydrogenation was continued for 2 hours. After completion of the reaction, the vessel was pressure purged with nitrogen (4×). The catalyst was removed from the reaction mixture by filtration through powdered cellulose. Methanol (10 g) was used to rinse the reaction vessel and the filter cake. The filtrate and wash were combined, and methanol was evaporated under reduced pressure at 30–40° C. The solution was reduced to 67 g total mass, and 4 g of deionized water was added. The solution was cooled to 30° C. and seeded with 0.02 g neotame crystals. The seeded solution was cooled over 5 hours to 5° C. The crystallized solid was isolated by filtration and washed with 20 ml deionized water. The wet product was dried under vacuum to give 6.30 g neotame (>98% by HPLC, 70% yield).

EXAMPLE 8

In a stirred hydrogenation vessel containing a solution of z-aspartame (15.0 g) and 5% palladium on carbon catalyst (containing 50% water) (2.0 g), methanol (100 ml) and water (75 ml) were added. After pressure purging the reactor with nitrogen (4x), followed by hydrogen (4x), the mixture was heated to 40° C. and pressurized to 50 psig with hydrogen. Over a period of one hour and 40 minutes, 3.46 g of 3,3-dimethylbutyraldehyde were pumped into the stirred reaction mixture. After addition of the aldehyde, hydrogenation was continued for 2 hours. After completion of the reaction, the vessel was pressure purged with nitrogen (4x). The mixture was filtered through a Celite bed, and the bed was washed with methanol (100 ml). The filtrate and wash were combined, and methanol was evaporated under reduced pressure at 30–35° C. The solution was reduced to about 80 ml. The solution was cooled to room temperature and seeded with 0.02 g neotame crystals. The seeded solution was cooled overnight to 5° C. The crystallized solid was isolated by filtration and washed with 25 ml cold water. The wet product was dried under vacuum to give 10.20 g neotame (>98% by HPLC, 78% yield).

COMPARATIVE EXAMPLE 1 (WO 00/15656)

Z-Aspartame (4.28 g) was dissolved in 50 ml of methanol in a hydrogenation reaction vessel. 3,3-Dimethylbutyraldehyde (1.0 g) and 5% palladium on carbon (containing 50% water) were added to the vessel. The reactor was rendered inert with the aid of $N_2$, after which the whole was heated to 40° C. and the nitrogen was replaced by bubbling of hydrogen. After 9 hours, the reaction was stopped. The catalyst was removed through filtration. The solution was concentrated through evaporation using the rotavaporator at 40° C. at a lowered pressure of 10 mm, after which water was added until a precipitate began to form. The mixture was heated to 50° C., which led to the formation of a clear solution. The solution was subsequently cooled to 10° C. overnight, after which the neotame crystallized as a white crystalline product. The solid product was separated via filtration and washed using successively: 3 ml water and 4x5 ml of heptane. The product was subsequently dried in a vacuum oven at room temperature. The product obtained contained, inter alia, 87.6% neotame, 2.26% dialkylated aspartame and 5.07% dialkylated imidazolidinone.

While the invention has been described in terms of preferred embodiments and specific examples, those skilled in the art will recognize through routine experimentation that various changes and modifications can be made without departing form the spirit and scope of the invention. Thus, the invention should be understood as not being limited by the foregoing detailed description, but as being defined by the appended claims and their equivalents.

What is claimed is:

1. A process of synthesizing N-[N-(3,3-dimethylbutyl)-L-α-aspartyl]-L-phenylalanine 1-methyl ester comprising reacting an isolated acid salt of L-α-aspartyl-L-phenylalanine 1-methyl ester and 3,3-dimethylbutyraldehyde in a solvent in the presence of a catalyst and hydrogen and in the absence of an acid for a time and at a temperature sufficient to produce N-[N-(3,3-dimethylbutyl)-L-α-aspartyl]-L-phenylalanine 1-methyl ester.

2. The process according to claim 1, wherein the acid salt of L-α-aspartyl-L-phenylalanine 1-methyl ester is selected from the group consisting of hydrobromic, sulfuric, phosphoric, citric, acetic and hydrochloric acid salts of L-α-aspartyl-L-phenylalanine 1-methyl ester.

3. The process according to claim 2, wherein the acid salt of L-α-aspartyl-L-phenylalanine 1-methyl ester is the hydrochloric acid salt of L-α-aspartyl-L-phenylalanine 1-methyl ester.

4. The process according to claim 1, wherein the catalyst is selected from the group consisting of platinum on activated carbon, palladium on activated carbon, platinum black, palladium black, nickel on silica, nickel on alumina, Raney nickel, ruthenium black, ruthenium on carbon, palladium hydroxide on carbon, palladium oxide, platinum oxide, rhodium black, rhodium on carbon and rhodium on alumina.

5. The process according to claim 4, wherein the catalyst is a palladium or platinum catalyst.

6. The process according to claim 1, wherein the weight ratio of catalyst on a dry basis to L-α-aspartyl-L-phenylalanine 1-methyl ester is from about 0.01:1 to about 0.25:1.

7. The process according to claim 6, wherein the weight ratio of catalyst on a dry basis to L-α-aspartyl-L-phenylalanine 1-methyl ester is about 0.10:1.

8. The process according to claim 1, wherein the solvent is selected from the group consisting of ethanol, ethyl acetate, acetonitrile, dioxane, isopropanol, methanol, isobutyl methyl ketone, tetrahydrofuran, cyclohexane, toluene, dimethylformamide, water and mixtures thereof.

9. The process according to claim 1, wherein the 3,3-dimethylbutyraldehyde is added gradually.

10. The process according to claim 1, wherein the 3,3-dimethylbutyraldehyde is added all at once.

11. The process according to claim 1, wherein the ratio of L-α-asparyl-L-phenylalanine 1-methyl ester to 3,3-dimethylbutyraldhyde is from about 1:0.95 to about 1:1.

12. The process according to claim 1, wherein the mixture is stirred while N-[N-(3,3-dimethylbutyl)-L-α-asparyl]-L-phenylalanine 1-methyl ester crystallizes.

13. The process according to claim 1, wherein the mixture is unstirred while N-[N-(3,3-dimethylbutyl)-L-α-aspartyl]-L-phenylalanine 1-methyl ester crystallizes.

14. The process according to claim 1, wherein the temperature sufficient to produce N-[N-(3,3-dimethylbutyl)-L-α-aspartyl]-L-phenylalanine 1-methyl ester is from about 20° C. to about 60° C.

15. The process according to claim 14, wherein the temperature sufficient to produce N-[N-(3,3-dimethylbutyl)-L-α-aspartyl]-L-phenylalanine 1-methyl ester is from about 22° C. to about 40° C.

16. The process according to claim 1, wherein the time sufficient to produce N-[N-(3,3-dimethylbutyl)-L-α-aspartyl]-L-phenylalanine 1-methyl ester is from about 1 hour to about 24 hours.

17. The process according to claim 16, wherein the time sufficient to produce N-[N-(3,3-dimethylbutyl)-L-α-aspartyl]-L-phenylalanine 1-methyl ester is from about 2 hours to about 4 hours after addition of the 3,3-dimethylbutyraldehyde.

18. The process according to claim 1, wherein the pressure of the hydrogen is from about 5 psi to about 100 psi.

19. The process according to claim 18, wherein the pressure of the hydrogen is from about 30 psi to about 50 psi.

20. A process of synthesizing N-[N-(3,3-dimethylbutyl)-L-α-aspartyl]-L-phenylalanine 1-methyl ester comprising reacting an admixture of N-protected L-α-aspartyl-L-phenylalanine 1-methyl ester and 3,3-dimethylbutyraldehyde in a solvent in the presence of a catalyst and in the presence of hydrogen for a time and at a temperature sufficient to produce N-[N-(3,3-dimethylbutyl)-L-α-aspartyl]-L-phenylalanine 1-methyl ester that is greater than 98% pure, wherein the 3,3-dimethylbutyraldehyde is added gradually.

21. The process according to claim 20, wherein the N-protected L-α-aspartyl-L-phenylalanine 1-methyl ester is selected from the group consisting of N-(p-methoxybenzyl)oxycarbonyl-L-α-aspartyl-L-phenylalanine 1-methyl ester, N-(p-chlorobenzyl)oxycarbonyl-L-α-aspartyl-L-phenylalanine 1-methyl ester, N-(p-bromobenzyl)oxycarbonyl-L-α-aspartyl-L-phenylalanine 1-methyl ester, N-(p-nitrobenzyl)oxycarbonyl-L-α-aspartyl-L-phenylalanine 1-methyl ester, N-benzyl-L-α-aspartyl-L-phenylalanine 1-methyl ester, N-formyl-L-α-aspartyl-L-phenylalanine 1-methyl ester and N-silyl-L-α-aspartyl-L-phenylalanine 1-methyl ester.

22. The process according to claim 20, wherein the catalyst is selected from the group consisting of platinum on activated carbon, palladium on activated carbon, platinum black, palladium black, nickel on silica, nickel on alumina, Raney nickel, ruthenium black, ruthenium on carbon, palladium hydroxide on carbon, palladium oxide, platinum oxide, rhodium black, rhodium on carbon and rhodium on alumina.

23. The process according to claim 22, wherein the catalyst is a palladium or platinum catalyst.

24. The process according to claim 20, wherein the weight ratio of catalyst on a dry basis to N-protected L-α-aspartyl-L-phenylalanine 1-methyl ester is from about 0.01:1 to about 0.25:1.

25. The process according to claim 24, wherein the weight ratio of catalyst on a dry basis to N-protected L-α-aspartyl-L-phenylalanine 1-methyl ester is about 0.10:1.

26. The process according to claim 20, wherein the solvent is selected from the group consisting of ethanol, ethyl acetate, acetonitrile, dioxane, isopropanol, methanol, isobutyl methyl ketone, tetrahydrofuran, cyclohexane, toluene, dimethylformamide, water and mixtures thereof.

27. The process according to claim 20, wherein the ratio of N-L-α-aspartyl-phenylalanine 1-methyl ester to 3,3-dimethylbutyraldehyde is from about 1:0.95 to about 1:1.

28. The process according to claim 20, wherein the mixture is stirred.

29. The process according to claim 20, wherein the mixture is unstirred.

30. The process according to claim 20, wherein the temperature sufficient to produce N-[N-(3,3-dimethylbutyl)-L-α-aspartyl]-L-phenylalanine 1-methyl ester is from about 20° C. to about 60° C.

31. The process according to claim 30, wherein the temperature sufficient to produce N-[N-(3,3-dimethylbutyl)-L-α-aspartyl]-L-phenylalanine 1-methyl ester is from about 22° C. to about 40° C.

32. The process according to claim 20, wherein the time sufficient to produce N-[N-(3,3-dimethylbutyl)-L-α-aspartyl]-L-phenylalanine 1-methyl ester is from about 1 hour to about 24 hours.

33. The process according to claim 32, wherein the time sufficient to produce N-[N-(3,3-dimethylbutyl)-L-α-aspartyl]-L-phenylalanine 1-methyl ester is from about 2 hours to about 4 hours after addition of the 3,3-dimethylbutyraldehyde.

34. The process according to claim 20, wherein the pressure of the hydrogen is from about 5 psi to about 100 psi.

35. The process according to claim 34, wherein the pressure of the hydrogen is from about 30 psi to about 50 psi.

* * * * *

UNITED STATES PATENT AND TRADEMARK OFFICE
CERTIFICATE OF CORRECTION

PATENT NO.    : 6,642,406 B2
DATED         : November 4, 2003
INVENTOR(S)   : Indra Prakash et al.

It is certified that error appears in the above-identified patent and that said Letters Patent is hereby corrected as shown below:

<u>Title page,</u>
Item [56], References Cited, FOREIGN PATENT DOCUMENTS, delete "WO 00/15656      3/2000"; and
OTHER PUBLICATIONS, "Anderson et al. . . .etc.", "sysnthesis" should read -- Synthesis --.

<u>Column 5,</u>
Line 31, "a-neotame" should read -- α-neotame --.

<u>Column 9,</u>
Line 54, "form" should read -- from --.

<u>Column 10,</u>
Line 37, "L-α-asparyl-L-" should read -- L-α-aspartyl-L- --; and
Line 40, "L-α-asparyl]-L-" should read -- L-α-aspartyl]-L- --.

Signed and Sealed this

Twenty-fifth Day of May, 2004

JON W. DUDAS
*Acting Director of the United States Patent and Trademark Office*